US005739300A

United States Patent [19]
Toepfer et al.

[11] Patent Number: 5,739,300
[45] Date of Patent: Apr. 14, 1998

[54] ANTIADHESIVE PIPERIDINE-AND PYRROLIDINECARBOXYLIC ACIDS

[75] Inventors: Alexander Toepfer, Kriftel; Gerhard Kretzschmar, Eschborn; Bernward Schölkens, Kelkheim; Peter Klemm, Wiesbaden; Christoph Hüls, Wackernheim; Dirk Seiffge, Mainz-Kostheim, all of Germany

[73] Assignee: Hoechst Aktiengesellschaft, Frankfurt, Germany

[21] Appl. No.: 726,142

[22] Filed: Oct. 4, 1996

[30] Foreign Application Priority Data

Oct. 9, 1995 [DE] Germany ............ 195 37 334.0

[51] Int. Cl.$^6$ ............ A61K 31/70; C07H 3/02; C07H 3/06; C07H 15/04
[52] U.S. Cl. ............ 536/4.1; 514/23; 514/25; 514/61; 514/247; 514/315; 514/317; 514/885; 536/18.5; 536/120; 536/123
[58] Field of Search ............ 514/23, 25, 61, 514/247, 315, 317, 885; 536/4.1, 18.5, 120, 123

[56] References Cited

FOREIGN PATENT DOCUMENTS 0 671 409   9/1995   European Pat. Off. .

OTHER PUBLICATIONS

T. Uchiyama et al., "Design and Synthesis of Sialyl Lewis X Mimetics", J. Am. Chem. Soc., vol. 117, (1995), pp. 5395–5396.
B.N. Narasinga Rao et al., "Sialyl Lewis X Mimics Derived from a Phamacophore Search are Selectin Inhibitors with Anti-Flammatory Activity", J. Biol. Chem. vol. 269, No. 31, Aug. (1994), pp. 19963–19666.
S. Hanessian et al., "Design and Synthesis of Glycomimetic Prototypes –A Model Sialyl Lewis$^x$ Ligand for E–Selectin", Synlett, No. 10, Oct. (1994), pp. 868–870.
Springer, Cell 76:301–314 (1994), "Traffic Signals for Lymphocyte Recirculation and Leudocyte Emigration: The Multistep Paradigm".
Mulligan et al., Nature 364:149–151 (1993), "Protective effects of oligosaccharides in P–selectin–dependent lung injury".
Buerke et al., J. Clin. Invest. 93:1140–1148 (1994), "Sialyl Lewis–containing Oligosaccharide Attenuates Myocardial Reperfusion Injury in Cats".
Jacob et al., Biochemistry 34:1210–1217 (1995), "Binding of Sialyl Lewis X to E–Selection As Measured by Fluorescence Polarization".

Brandley et al., Glycobiology 3(6):633–639 (1993), "Structure–function studies on selectin carbohydrate ligands. Modification to fucose, sialic acid and sulphate as a sialic acid replacement".
Yoshida et al., Glycoconjugate Journal 10:3–15 (1993), "Synthesis of chemically modified sialic acid–containing sialyl–Le$^x$ ganglioside analogues recognized by the selectin family".
Nelson et al., J. Clin. Invest., 91:1157–1166 (1993), "Higher–Affinity Oligosaccharide Ligands for E–Selectin".
Musser et al., Pharmacochem. Libr. vol. 20 (1993), Trends in Drug Res. Seiten 33–40, "Structure–Activity Sutdies Based on the Sialyl Lewis X Epitope".
Ausubel et al., Cureent Protocols in Molecular Biology, John Wiley, New York, vol. 2 Chapter 16, Protein Expression (1994).
Aruffo et al., Cell, 37:35–44 (1991), "CD62/P–Selectin Recognition of Myeloid and Tumor Cell Sulfatides".
Zettlmeissl et al., DNA and Cell Biology, 9(5):347–353 (1990), "Expression and Characterization of Human CD4: Immunoglobulin Fusion Proteins".
Walz et al., Science, 250:1132–1135 (1990), "Recognition by ELAM–1 of the Sialyl–Le$^x$ Determinant on Myeloid and Tumor Cells".
Springer, Nature, 346:425–434 (1990), "Adhesion receptors of the immume system".
Atherton et al., J. Physiol., 222:447–474 (1972), "Quantitative Investigations of the Adhesiveness of Circulationg Polymorphonuclear Leucocytes to Blood Vessel Walls".
Menger et al., Immunology Today, 14(11):519–522 (1993), "Scope and perspectives of intravital microscopy–bridge ofver in vitro to in vivo".
Foster et al., Agent Actions, 38 Special Conferece Issue (1993), "Production of TNFα by LPS–stimulated murine, rat and human blood and its pharmacological modulation".

Primary Examiner—John Kight
Assistant Examiner—Howard C. Lee
Attorney, Agent, or Firm—Foley & Lardner

[57] ABSTRACT

The invention relates to conjugates which consist of mono- or polycarboxylated piperidine or pyrrolidine derivatives and pyranoses, furanoses or polyalcohols linked via a chain or a cyclic system. The carboxyl groups of the piperidine derivatives can either be located directly on the ring or linked to the ring via a short chain. The invention additionally relates to the preparation of these compounds and to their use for the production of pharmaceuticals and diagnostics.

37 Claims, No Drawings

ANTIADHESIVE PIPERIDINE-AND PYRROLIDINECARBOXYLIC ACIDS

The invention relates to conjugates which consist of mono- or polycarboxylated piperidine or pyrrolidine derivatives and pyranoses, furanoses or polyalcohols linked via a chain or a cyclic system. The carboxyl groups of the piperidine derivatives can either be located directly on the ring or linked to the ring via a short chain. The invention additionally relates to the preparation of these compounds and to their use for the production of pharmaceuticals and diagnostics.

The circulation of blood cells such as, for example, leukocytes, neutrophils, granulocytes and monocytes at the molecular level is a multistage, very complex process which is only known in individual stages (Review: T. A. Springer, Cell 76, 301–314, 1994).

The most recent research results showed that the recirculation of the lymphocytes which is crucial in immunological surveillance and also the localization of neutrophils and monocytes at inflammation foci obey very similar molecular mechanisms. Thus in acute and chronic inflammation processes adhesion of the leukocytes to endothelial cells and migration into the inflammation focus and into the secondary lymphatic organs occurs.

In this process, numerous specific signal molecules such as, for example, interleukins, leukotrienes and tumor necrosis factor (TNF), their G protein-coupled receptors and, in particular, tissue-specific cell adhesion molecules are involved, which guarantee a precisely controlled recognition of the immune and endothelial cells. The most important adhesion molecules involved in this context, which in the following are to be described as receptors, include the selectins (E-, P- and L-selectins), integrins and the members of the immunoglobulin superfamily. The three selectin receptors determine the initial phase of leukocyte adhesion. E-selectin is expressed on endothelial cells a few hours after stimulation, for example by interleukin-1 (IL-1β) or tumor necrosis factor (TNF-α), whereas P-selectin is stored in blood platelets and endothelial cells and, after stimulation by thrombin, peroxide radicals or substance P, is presented, inter alia, on the cell surfaces. L-selectin is continuously expressed on leukocytes, but in the course of the inflammation is rapidly eliminated again from the leukocytes.

The adhesion of leukocytes to endothelial cells which is mediated in the initial phase of inflammatory processes by selectin receptors is a natural and necessary immune response to various inflammatory stimuli and injuries of the vascular tissue. The course of a number of acute and chronic disorders, however, is unfavorably affected by the excessive adhesion of leukocytes and their infiltration into the tissue affected and also by the damage to healthy tissue in the sense of an autoimmune reaction. These include, for example, rheumatism, reperfusion injuries such as myocardial ischemia/infarct (MI), acute pulmonary inflammation after surgical intervention, traumatic shock and stroke, psoriasis, dermatitis, ARDS (adult respiratory distress syndrome) and the restenosis occuring after surgical interventions (examples: angioplasty and by-pass operations).

The natural ligand with the structure of SLeX has already been successfully used in animal experiments in P-selectin-dependent lung injuries (M. S. Mulligan et al., Nature 1993, 364, 149) and in myocardial reperfusion injuries (M. Buerke et al., J. Clin. Invest. 1994, 93, 1140). In initial clinical tests on acute pulmonary inflammation, the compound is to be employed in a dose of 1–2 grams per day per patient (communication from Cytel Corp./La Jolla (Calif.) at the 2nd Glycotechnology Meeting/CHI in La Jolla/U.S.A. on May 16–18th 1994).

This high active compound dose is in accord with the known weak affinity of the natural SleX/A ligands for the selectin receptors. Thus SLeX in all known in vitro test systems inhibits cell adhesion to selectin receptors only at a relatively high concentration in the range of $IC_{50}$ about 1 mM (Jacob et al., Biochemistry 1995, 34, 1210). In some publications and patent applications attempts have meanwhile been reported to obtain more firmly binding antagonists by structural variation of the ligand. The aim of these studies is the provision of more effective antagonists which would also be potentially employable in vivo at a lower dose.

The variation of the fucose and neuraminic acid units until now regarded as crucial for the structure-activity relationship (B. K. Brandley et al., Glycobiology 1993, 3, 633 and M. Yoshida et al., Glycoconjugate J. 1993, 10, 3) did not produce, however, any significantly improved inhibition values. Solely on variation of the glucosamine unit (replacement of GlcNAc by glucose and azido and amino groups in the 2 position of GlcNAc) could a significantly increased affinity to the E-selectin receptor be achieved. In the P-selectin receptor, on the other hand, improved binding was not achieved.

For the inhibition of the adhesion of HL-60 and U-937 cells, the $IC_{50}$ data of these oligosaccharide derivatives should be 0.12 mM (compared with 1.2–2.0 mM for SLeX) in the case of E-selectin. It is a disadvantage, however, that the binding to L- and P-selectins is strongly adversely affected at >5 mM (Dasgupta et al., poster presentation from Glycomed Inc. on the occasion of the meeting in La Jolla in 5/94).

Generally, all successes in improving the binding affinity of SLeX and SLeA derivatives to the E-selectin receptor remained restricted, for with the P-selectin receptor only weak inhibition effects were found at inhibitor concentrations of about 1 mM (R. M. Nelson et al., J. Clin. Invest. 1993, 91, 1157).

The prior art on the binding affinity of modified SLeX/A structures to selectins is described in Pharmacochem. Libr. 1993, 20 (Trends in Drug Research), pages 33–40.

The object of the present invention consists in the preparation of novel selectin ligands which, in comparison to the natural ligands, have a distinctly stronger binding to the receptors and additionally can be synthesized more easily than these.

The object set is achieved by a compound of the formula I

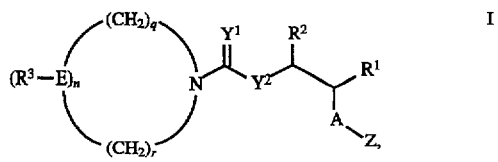

in which

Z is a pyranoside, a pyranosyl radical linked via the C6 position, an alkyl pyranoside linked via the C6 position, a furanoside, a furanosyl radical linked via the C5 position, an alkyl furanoside linked via the C5 position or a polyalcohol which is linked to A via any desired position, A is oxygen, —$CH_2$— or sulfur, $R^1$ and $R^2$ independently of one another are hydrogen, —$(CH_2)_m X^1$ or $CH_2O(CH_2)_m X^2$, where m is an integer from 1 to 20, or together are a five- or six-membered carbo- or heterocycle having at least one of the substituents $R^4$, $R^5$ or $R^6$, E is nitrogen, carbon or —CH—, $R^3$ is —$(CH_2)_p$COOH, (—COOH)$_2$, —$(CH_2)_p$CH(COOH)$_2$, —$(CH_2)_p$CNH$_2$(COOH)$_2$, —$(CH_2)_p$C(CH$_2$—C$_6$H$_5$)(COOH)$_2$, —CONHC(COOH)$_2$, where p is an integer from 0 to 10, or

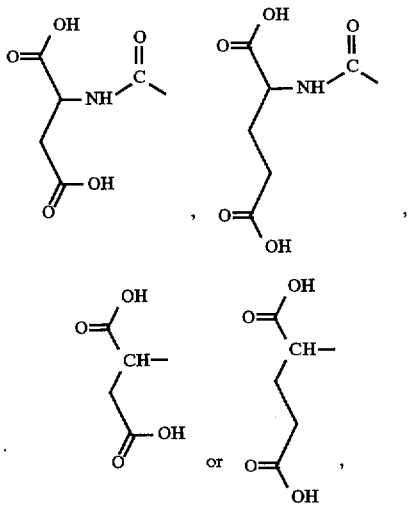

q and r independently of one another are an integer from 0 to 3, n is an integer from 1 to 3, with the proviso that the sum of q, r and n is 4 or 5, $R^4$, $R^5$ and $R^6$ independently of one another are H, OH, —O(CH$_2$)$_w$X$^3$ or CH$_2$O(CH$_2$)$_w$X$^4$, where w is an integer from 1 to 18, $Y^1$ and $Y^2$ independently of one another are oxygen, —NH— or sulfur and $X^1$, $X^2$, $X^3$ and $X^4$ independently of one another are hydrogen, —NH$_2$, —COOH, —OH, —CH$_2$OH, CH$_2$NH$_2$, —C$_1$-C$_{20}$-alkyl or —C$_6$-C$_{10}$-aryl.

The compound of the formula I is preferred wherein $R^1$ and $R^2$ together form a cyclohexane ring or together form a cyclopentane ring. Preferably, A, $Y^1$ and $Y^2$ in formula I are oxygen.

Particularly preferred compounds according to the present invention are furthermore distinguished in that Z in formula I is a pyranoside, preferably an L-fucoside, a D-mannoside, L-rhamnoside, L-galactoside or an L-mannoside.

Compounds of the formula I are also particularly suitable wherein Z is a furanoside, preferably a riboside.

Further preferred embodiments of the present invention are distinguished in that Z in formula I is a D-mannosyl radical linked via the C6 position or a methyl D-mannoside linked in the same way. Z in formula I is preferably also an L-threit-1-yl radical.

Preferred embodiments of the heterocycle formed from N (nitrogen), (CH$_2$)$_q$, (CH$_2$)$_r$ and ($R^3$-E)$_n$ in formula I are distinguished in that n is 1 and q and r are 2, n and r are 1 and q is 3 or n is 1, q is 0 and r is 3. The substituent $R^3$ in formula I is preferably —(CH$_2$)$_p$COOH, where p is 0, or —(CH$_2$)$_p$CH(COOH)$_2$, where p is 1, in both cases the variable E preferably being —CH—. $R^3$ is preferably also (—COOH)$_2$, where E is carbon.

Examples of compounds having the preferred properties mentioned are shown below.

1. A compound of the formula I, which is distinguished in that

Z is a pyranoside, for example an L-fucoside, and

A, $Y^1$ and $Y^2$ are oxygen, $R^1$ and $R^2$ together form a cyclohexane ring, $R^3$ is (CH$_2$)$_p$COOH, E is —CH—, n is 1, q and r are 2 and p is 0, for example

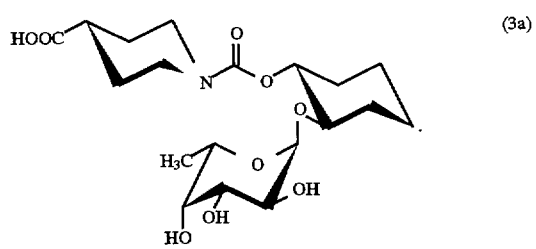

(3a)

2. A compound of the formula I, which is distinguished in that

Z is a pyranoside, for example an L-fucoside, and

A, $Y^1$ and $Y^2$ are oxygen, $R^1$ and $R^2$ together form a cyclohexane ring, $R^3$ is (CH$_2$)$_p$CH(COOH)$_2$, E is —CH—, n and r are 1, q is 3 and p is 1, e.g.

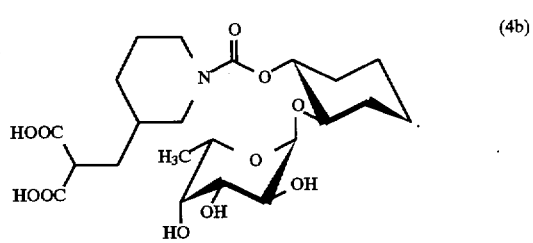

(4b)

3. A compound of the formula I, which is distinguished in that

Z is a pyranoside, for example an L-fucoside, and

A, $Y^1$ and $Y^2$ are oxygen, where $R^1$ and $R^2$ together form a cyclohexane ring, $R^3$ is (COOH)$_2$, E is carbon, n is 1 and q and r are 2, for example

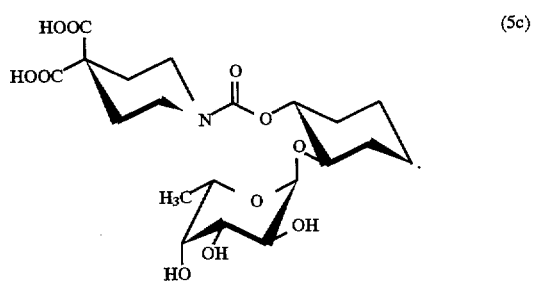

(5c)

4. A compound of the formula I, which is distinguished in that

Z is a pyranoside, for example an L-rhamnoside, and

A, $Y^1$ and $Y^2$ are oxygen,
$R^1$ and $R^2$ together form a cyclohexane ring,
$R^3$ is $(CH_2)_p COOH$, E is —CH—, p is 0,
n is 1 and
q and r are 2, for example

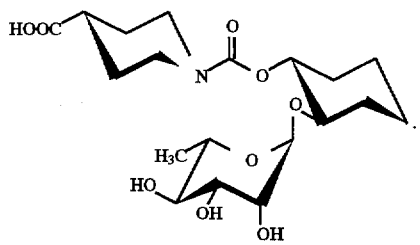
(3d)

5. A compound of the formula I, which is distinguished in that

Z is a pyranoside, for example an L-fucoside, and
A, $Y^1$ and $Y^2$ are oxygen, where
$R^1$ and $R^2$ together form a cyolopentane ring, and
$R^3$ is $(CH_2)_p COOH$, E is —CH—, p is 0,
n is 1 and
q and r are 2, for example

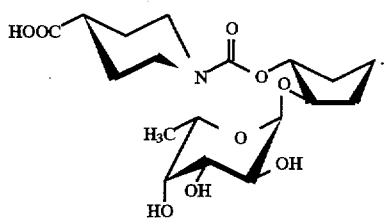
(1e)

6. A compound of the formula I, which is distinguished in that

Z is a pyranoside, for example an L-fucoside, and
A, $Y^1$ and $Y^2$ are oxygen, where
$R^1$ and $R^2$ together form a cyclohexane ring and
$R^3$ is $(CH_2)_p CH(COOH)_2$, p is 1, E is —CH—,
n is 1,
q is 0 and
r is 3, for example

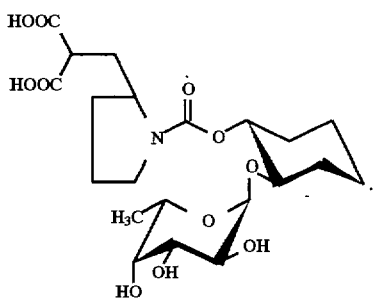
(1g)

Further examples are compounds of the formula I, which are distinguished in that
$R^1$ and $R^2$ together form a cyclohexane ring and
A, $Y^1$ and $Y^2$ are oxygen, where
n is 1,
q and r are 2,
$R^3$ is $(CH_2)_p COOH$, E is —CH—, p is 0 and 7. Z is an L-threit-1-yl radical, e.g.

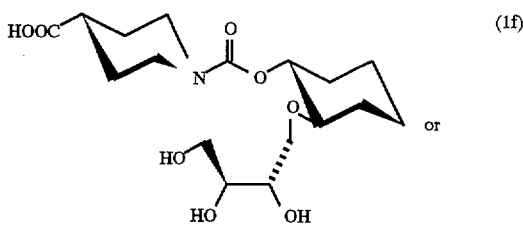
(1f)

Z is an alkyl pyranoside linked via the $C_6$ position, 8. for example a methyl α-D-mannopyranoside,

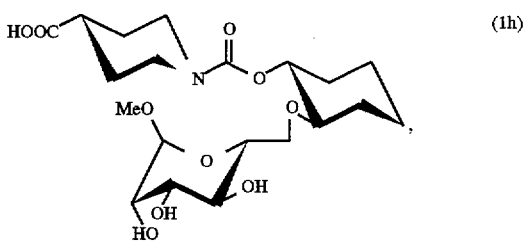
(1h)

or 9. for example a methyl β-D-galactopyranoside

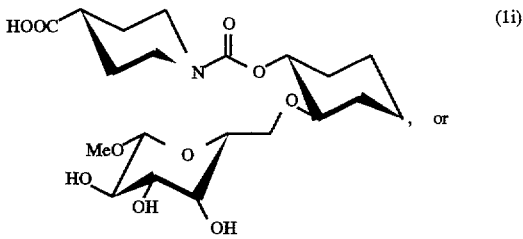
(1i)

10. Z is a pyranosyl radical linked via the $C_6$ position, for example a galactosyl radical, e.g.

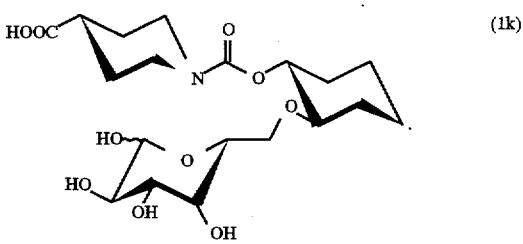
(1k)

The object set at the outset is furthermore solved by a process for the preparation of a compound of the formula I, which is distinguished in that first, by O- or S-glycosylation, alkylation or C—C linkage of a functional group of an acceptor of the formula II

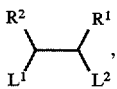

II having at least two adjacent functional groups $L^1$ and $L^2$ and also having the substituents $R^1$ and $R^2$, by means of an equivalent of a donor, provided with an activating group $L^3$ and, if appropriate, with protective groups, of the formula III

    III intermediate compound IV

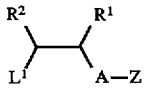    IV is prepared, after which, by reaction with a reagent of the formula V

    V in which $L^4$ and $L^5$ have the meaning of leaving groups, the activated compound VI

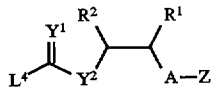    VI is obtained, which is converted by reaction with a mono- or polycarboxylated cyclic amine or a suitable precursor thereof and, if appropriate, after cyclization or carboxylation and also after elimination of protective groups, to the compound of the formula I, the variables $R^1$, $R^2$, $Y^1$, $Y^2$, A and Z having the meanings mentioned.

The compounds of the formula I according to the invention can be prepared starting from commercially available components having at least 2 adjacent functional groups (acceptor II), such as, for example, (1R,2R)-trans-1,2-cyclohexanediol or tri-O-acetyl-D-glucal. In these compounds, for example (in the first case) by glycosylation with a carbohydrate donor (e.g. trichloroacetimidate, ethyl thioglycoside etc.) or alkylation with an activated polyalcohol (e.g. tosylate of 1,2,3-tri-O-benzyl-L-threitol), the first of the two adjacent functional groups (e.g. a hydroxyl group) can be reacted (intermediate compound IV). The still remaining functional group ($L^1$, e.g. likewise a hydroxyl group) can then be reacted, for example, with nitrophenyl chloroformate (reagent of the formula V having the leaving groups Cl and O—$C_6H_4$—$NO_2$) to give the nitrophenyl carbamate (compound VI), which then reacts in the same reaction vessel with a cyclic amine (e.g. ethyl piperidine-4-carboxylate) or a suitable precursor [e.g. 3-(hydroxymethyl) piperidine] to give compounds of the formula I or to give their precursors (see Example 4b).

Despite their substantially lower molar mass than sialyl Lewis X, the compounds of the formula I according to the invention can have a higher affinity than this for the natural receptors, for example for E- and P- selectin. This can be detected with the aid of the cell adhesion assays described below.

Primary assays for the investigation of the action of the compounds of the present invention for cell adhesion to recombinant, soluble selectin fusion proteins.

In order to test the activity of the compounds according to the invention on the interaction between the E- and P-selectins (old nomenclature ELAM-1 and GMP-140) with their ligands, an assay is used which is only specific for one of these interactions in each case. The ligands are supplied in their natural form as surface structures on promyelocytic HL60 cells. As HL60 cells have ligands and adhesion molecules of very different specificity, the desired specificity of the assay can only be produced by means of the binding component. The binding components used were genetically engineered soluble fusion proteins from the extracytoplasmic domain of E- or P-selectin in each case and the constant region of a human immunoglobulin of the subclass IgG1.

Preparation of L-selectin-IgG1

To prepare soluble L-selectin-IgG1 fusion protein, the genetic construct "ELAM-Rg" published by Walz et al., 1990 was used.

For expression, the plasmid DNA was transfected in COS-7 cells (ATCC) by means of DEAE-dextran (Molecular biological methods: see Ausubel, F. M., Brent, R., Kingston, R. E., Moore, D. D., Seidman, J. G., Struhl, K. and Smith, J. A. 1990. Current Protocols in Molecular Biology, John Wiley, New York). Seven days after transfection, the culture supernatant is recovered, freed from cells and cell fragments by centrifugation and transferred to 25 mM HEPES pH 7.0, 0.3 mM PMSF, 0.02% sodium azide and kept at +4° C. (Walz, G., Aruffo, A., Kolanus, W., Bevilacqua, M. and Seed, B. 1990. Recognition by ELAM-1 of the sialyl-Lex determinant on myeloid and tumor cells. Science 250, 1132–1135.)

Preparation of P-selectin-IgG1

To prepare the soluble P-selectin-lgG1 fusion protein, the genetic construct "CD62Rg" published by Aruffo et al., 1991 is used. The further procedure corresponds to the preparation of L-selectin-IgG1 presented under A1.

Aruffo, A., Kolanus, W., Walz, G., Fredman, P. and Seed, B. 1991. CD62/P-Selectin recognition of myeloid and tumor cell sulfatides. Cell 67, 35–44.

Preparation of CD4-lgG1

To prepare the soluble CD4-lgG1 fusion protein, the genetic construct "CD4:IgG1 hinge" published by Zettelmeissl et al., 1990 is used. The further procedure corresponds to the preparation of L-selectin-lgG1 presented under A1. (Zettelmeissl, G., Gregersen, J.-P., Duport, J. M., Mehdi, S., Reiner, G. and Seed, B. 1990. Expression and characterization of human CD4: Immunoglobulin Fusion Proteins. DNA and Cell Biology 9, 347–353.)

Carrying out the HL60 cell adhesion assays on recombinant, soluble adhesion molecules 1. 96-well microtiter test plates (Nunc Maxisorb) are incubated at room temperature for 2 hours with 100 μl of a goat anti-human IgG antibody (Sigma) diluted (1+100) in 50 mM tris pH 9.5. After removing the antibody solution, washing is carried out once with PBS.

2. 150 μl of the blocking buffer are left in the wells for 1 hour at room temperature. The composition of the blocking buffer is: 0.1% gelatin, 1% BSA, 5% calf serum, 0.2 mM PMSF, 0.02% sodium azide. After removing the blocking buffer, washing is carried out once with PBS.

3. 100 μl each of cell culture supernatant of correspondingly transfected and expressing COS cells are pipetted into the wells. Incubation is carried out for 2 hours at room temperature. After removing the cell culture supernatant, washing is carried out once with PBS.

4. 20 μl of binding buffer are added to the wells. The binding buffer has the composition: 50 mM HEPES, pH 7.5; 100 mM NaCl; 1 mg/ml BSA; 2 mM $MgCl_2$; 1 mM $CaCl_2$; 3 mM $MnCl_2$; 0.02% sodium azide; 0.2 mM PMSF. To do this, 5 μl of the test substance are pipetted, mixed by swirling the plate and incubated at room temperature for 10 min.

5. 50 ml of a HL60 cell culture having 200,000 cells/ml are centrifuged at 350 g for 4 min. The pellet is resuspended in 10 ml of RPMI 1640 and the cells are centrifuged again. To label the cells, 50 µg of BCECF-AM (Molecular Probes) are dissolved in 5 µl of anhydrous DMSO; 1.5 ml of RPMI 1640 are then added to the BCECF-AM/DMSO solution. Using this solution, the cells are resuspended and incubated at 37° C. for 30 min. After centrifugation at 350 g for 2 minutes, the labeled cell pellet is resuspended in 11 ml of binding buffer and the resuspended cells are divided into 100 µl aliquots in the microtiter plate wells. The plate is allowed to stand at room temperature for 10 min in order to allow the cells to sediment on the bottom of the test plate. During the course of this, the cells have the opportunity to adhere to the coated plastic.

6. To stop the test, the microtiter plate is completely immersed in the stop buffer (25 mM tris, pH 7.5; 125 mM NaCl; 0.1% BSA; 2 mM $MgCl_2$; 1 mM $CaCl_2$; 3 mM $MnCl_2$; 0.02% sodium azide) at an angle of 45°. By inversion, the stop buffer is removed from the wells and the procedure is repeated again twice.

7. The measurement of the BCECF-AM-labeled cells adhering in the wells is carried out in a cytofluorimeter (Millipore), at a sensitivity setting of 4, an excitation wavelength of 485/22 nm and an emission wavelength of 530/25 nm.

Results:

IC 50 values for E-selectin [mM], in round brackets for P-selectin [mM]: N-Carbonyl-4-carboxypiperidyl-(1→2)-[(α-L-fucopyranosyl)-(1→1)]-(1R, 2R)-trans-1,2-cyclohexanediol (3a):

greater than 2 (greater than 2)

[N-Carbonyl-(1,1-dicarboxyl-ethyl)-(2→3)-piperidyl]-(1→2)-[(α-L-fuco-pyranosyl)-(1→1)]-(1R, 2R)-trans-1,2-cyclohexanediol (4b): greater than 2 (greater than 2) N-Carbonyl-4-carboxypiperidyl-(1→2)-[(α-L-fucopyranosyl)-(1→1)]-(1R, 2R)-trans-1,2-cyclopentanediol (1e):

3.7 (2.85)

N-Carbonyl-4,4-dicarboxypiperidyl-(1→2)-[(α-L-fucopyranosyl)-(1→1)]-(1R, 2R)-trans-1,2-cyclohexanediol (3e):

1.6 (7.5)

Leukocyte adhesion—Testing of the activity of the compounds according to the invention in vivo (intravital microscopy in the rat):

In inflammatory processes and other conditions activating the cytokines, tissue destruction due to leukocytes migrating in or blocking the microcirculation plays a crucial part. The first phase, which is crucial for the further process of the disease, is the activation of leukocytes within the blood stream, in particular in the pre- and postcapillary region. After the leukocytes have left the axial flow of the blood, a first adhesion of the leukocytes to the vascular inner wall, i.e. to the vascular endothelium, occurs here. All following leukocyte effects, i.e. active migration through the vessel wall and subsequent oriented migration in the tissue, are secondary reactions (Harlan, J. M., Leukocyte-endothelial interaction, Blood 65, 513–525, 1985).

This receptor-mediated interaction of leukocytes and endothelial cells is regarded as an initial sign of the inflammation process. In addition to the adhesion molecules already physiologically expressed, under the action of inflammation mediators (leukotrienes, PAF) and cytokines (TNF-alpha, interleukins), a temporally graded, massive expression of adhesion molecules occurs on the cells. They are at present divided into three groups: 1. immunoglobulin gene superfamily, 2. integrins and 3. selectins. While adhesion takes place between molecules of the Ig gene superfamily and the protein-protein bonds, in the cooperation between selectins lectin-carbohydrate bonds are prominent (Springer, T. A., Adhesion receptors of the immune system. Nature 346,425–434, 1990; Huges, G., Cell adhesion molecules—the key to an universal panacea, Scrips Magazine 6, 30–33, 1993; Springer, T. A., Traffic signals for lymphocyte recirculation and leukocyte emigration; The multistep paradigm. Cell 76, 301–314, 1994).

Method:

The induced adhesion of leukocytes is quantified in the mesenterium of the rat using an intravital microscopic investigation technique (Atherton A. and Born G. V. R., Quantitative investigations of the adhesiveness of circulating polymorphonuclear leukocytes to blood vessel walls. J. Physiol. 222, 447–474, 1972; Seiffge, D. Methoden zur Untersuchung der Rezeptor-vermittelten Interaktion zwischen Leukozyten und Endothelzellen im Entzündungsgeschehen [Methods for investigation of the receptor-mediated interaction between leukocytes and endothelial cells in inflammatory phenomena], in: Ersatz- und Ergänzungsmethoden zu Tierversuchen in der biomedizinischen Forschung [Substitution and replacement methods for animal experiments in biomedical research], Schöffl, H. et al., (ed.) Springer, 1995 (in print)). Lasting anesthesia is initiated under inhalation ether anesthesia by intramuscular injection of urethane (1.25 mg/kg of body weight). After exposing vessels (femoral vein for the injection of substances and carotid artery for blood pressure measurement), catheters are tied into them. After this, the corresponding transparent tissue (mesenterium) is exposed by the standard methods known in the literature and arranged on the microscope stage and coated with warm liquid paraffin at 37° C. (Menger, M. D. and Lehr, H, A., Scope and perspectives of intravital microscopy-bridge over from in vitro to in vivo, Immunology Today 14, 519–522, 1993). The administration of the test substance to the animals is carried out i.v. (10 mg/kg). The experimental increase in blood cell adhesion is induced by cytokine activation by systemic administration of lipopolysaccharide (LPS, 15 mg/kg) 15 minutes after administration of test substance (Foster S. J., Mc Cormick L. M., Ntolosi B. A. and Campbell D., Production of TNF-alpha by LPS-stimulated murine, rat and human blood and its pharmacological modulation, Agents and Actions 38, C77-C79, 1993, 18.01.1 995). The increased adhesion of leukocytes to the endothelium caused by this means is quantified by direct vital microscopy or with the aid of fluorescent dyes. All measuring operations are recorded by video camera and stored on a video recorder. Over a period of 60 minutes, the number of rolling leukocytes (i.e. all visibly rolling leukocytes which are slower than the flowing erythrocytes) and the number of leukocytes adhering to the endothelium (residence period longer than 5 seconds) is determined every 10 minutes. After completion of the experiment, the anesthetized animals are painlessly put to sleep without excitation by systemic injection of T61. For analysis, the results of 8 treated animals are in each case compared (details of the results in percentages) with 8 untreated animals (control group).

Results:

3a: Dose: 10 mg/kg; administration: i.v.; species: SPRD (m); weight in g: 298+/−17.72; number of vessels: 15; vessel diameter in µm 24+/−5; leukocytes in $10^3/mm^3$ 7.7 +/−2.66; fibrinogen in mg/100 ml: 135+/−21.71; inhibition: 81%.

Dose: 5 mg/kg; administration: i.v.; species: SPRD (m); weight in g: 306+/−6.65; number of vessels: 16; vessel diameter in μm 27+/−4; leukocytes in $10^3/mm^3$:7.5 +/−1.93; fibrinogen in mg/100 ml 101+/−5.75; inhibition: 69%.

Dose: 1 mg/kg; administration: i.v.; species: SPRD (m); weight in g: 333+/−21.6; number of vessels: 16; vessel diameter in μm 25 +/−4.1; leukocytes in $10^3/mm^3$:7.3+/−1.4; fibrinogen in mg/100 mh 117+/−15.8; inhibition: 64%.

Reperfusion model for investigation of the effects of the adhesion of neutrophils in the course of ischemia/reperfusion on the open rabbit heart The hearts are perfused at constant pressure according to the Langendorff technique with nutrient solution and also with/without leukocytes or active compound. Ischemia is then produced by tying off the left coronary artery (30 min). After reperfusion (30 min), the leukocyte accumulation is histologically assessed. In the course of the experiment, potentials and arrhythmias are additionally measured on 256 electrodes (total time of experiment about 90 min). In 6 of 7 untreated hearts perfused with leukocytes, pronounced arrhythmias occur as a result of leukocyte infiltration, while the hearts treated with active compound (RGDS peptides, chondroitin sulfate) develop reduced leukocyte accumulation and arrhythmias. The compound 3a investigated was highly active in the range from about 1 μM (considerable reduction of arrhythmias).

The compounds according to the present invention and their physiologically tolerable salts are very highly suitable on account of their useful pharmacological properties for use as therapeutics in mammals, in particular man.

The present invention therefore furthermore relates to a pharmaceutical comprising at least one compound as in formula I and its use for the production of a pharmaceutical for the therapy or prophylaxis of illnesses which are associated with excessive cell adhesion, mediated by selectin receptors, in the tissue affected by the illness, for example rheumatism, cardiovascular disorders, such as reperfusion injuries, ischemia or cardiac infarct.

The pharmaceuticals are particularly suitable for the treatment of acute and chronic inflammations which can be characterized pathophysiologically by a disorder of the cell circulation, for example of lymphocytes, monocytes and neutrophilic granulocytes. These include autoimmune disorders such as acute polyarthritis, rheumatoid arthritis and insulin-dependent diabetes (diabetes mellitus IDDM), acute and chronic transplant rejections, shock lung (ARDS, adult respiratory distress syndrome), inflammatory and allergic skin disorders such as, for example, psoriasis and contact eczema, cardiovascular disorders such as myocardial infarct, reperfusion injuries after thrombolysis, angioplasty or by-pass operations, septic shock and systemic shock. A further potential indication is the treatment of metastasizing tumors, since tumor cells carry surface antigens which have both sialyl-Lewis-X and sialyl-Lewis-A structures as recognition epitopes. Moreover, these pharmaceuticals, which are stable in the acidic medium of the stomach, can be employed for the antiadhesive therapy of Helicobaoter pylori and related microorganisms, if appropriate also in combination with antibiotics. Furthermore, with the aid of these pharmaceuticals a therapy of the cerebral form of malaria is conceivable.

In general, the pharmaceuticals according to the invention are administered intravenously, orally or parenterally or as implants, but rectal administration is also possible in principle. Suitable solid or liquid pharmaceutical preparation forms are, for example, granules, powders, tablets, coated tablets, (micro)capsules, suppositories, syrups, emulsions, suspensions, aerosols, drops or injectable solutions in ampoule form and also preparations halving a protracted release of active compound, in whose preparation excipients and additives and/or auxiliaries such as disintegrants, binders, coating agents, swelling agents, gildants or lubricants, flavorings, sweeteners or solubilizers are customarily used. Frequently used excipients or auxiliaries which may be mentioned are, for example, magnesium carbonate, titanium dioxide, lactose, mannitol and other sugars, talc, milk protein, gelatin, starch, vitamins, cellulose and its derivatives, animal and vegetable oils, polyethylene glycols and solvents, such as, for example, sterile water, alcohols, glycerol and polyhydric alcohols.

The pharmaceutical preparations are preferably prepared and administered in dose units. Solid dose units are tablets, capsules and suppositories. Depending on the efficacy of the compound, the type of administration, nature and severity of the disorder, age and body weight of the patient, different daily doses are necessary for the treatment of a patient. Under certain circumstances, however, higher or lower daily doses may also be appropriate. The daily dose can be administered both by single administration in the form of a single dose unit or else of several small dose units and by multiple administration of divided doses at specific intervals. The daily dose to be administered may additionally be dependent on the number of receptors expressed during the course of the illness. It is conceivable that in the initial stage of the illness only a few receptors on the cell surface are expressed and accordingly the daily dose to be administered is lower than in severely ill patients.

The pharmaceuticals according to the invention are prepared by bringing a compound of the present invention into the or a suitable administration form using customary excipients and also, if appropriate, additives and/or auxiliaries.

The use of compounds of the formula I for the production of a composition for the diagnosis of an illness which is associated with excessive cell adhesion, mediated by selectin receptors, in the tissue affected by the illness is furthermore conceivable.

Examples of the preparation of the compounds according to the invention:

EXAMPLE 1 a) Synthesis of [(2,3,4-tri-O-benzyl-α-L-fucopyranosyl)-(1→1)]-(1R, 2R)-trans-1,2-cyclohexanediol (1a):

A mixture of (1R,2R)-trans-1,2-cyclohexanediol (2.43 g, 20.9 mmol), thioethyl O-2,3,4-tri-O-benzyl-β-L-fucopyranoside (8.0 g, 16.72 mmol) and tetrabutylammonium bromide (2.7 g, 8.36 mmol) in dichloromethane (200 ml) and DMF (40 ml) is stirred with molecular sieve 4 A for 1 h. Copper(II) bromide (5.6 g, 25.08 mmol) is then added. After 24 h, the mixture is filtered through kieselguhr, and washed with saturated sodium hydrogen carbonate solution and then with saturated sodium chloride solution. The organic phase is dried over magnesium sulfate, concentrated in vacuo and chromatographed using hexane/ethyl acetate 3:1. Yield: 6.8 g, 76%. $^1$H-NMR (300 MHz, CDCl$_3$):δ=1.13 (d, 3H, 6-H$_{fuc}$), 1.21 (m, 4H, 4-H$_{cyclohex}$, 5-H$_{cyclohex}$), 1.65, 2.01 (2m, 4H, 3-H$_{cyclohex}$, 6-H$_{cyclohex}$)

b) Synthesis of N-carbonyl-4-carbethoxypiperidyl-(1→2)-[(2,3,4-tri-O-benzyl-α-L-fucopyranosyl)-(1→1)]-(1R,2R)-trans-1,2-cyclohexane-diol (2a):

Triethylamine (2.3 ml, 16.9 mmol), DMAP (206 mg, 1.69 mmol) and nitrophenyl chloroformate (3.1 g, 15.39 mmol) are added at 0° C. to a solution of 1a (8.2 g, 15.39 mmol) in dichloromethane (164 ml). The mixture is stirred overnight and treated with N-ethyldiisopropylamine (4.6 ml, 26.9 mmol) and ethyl piperidine-4-carboxylate (4.15 ml, 26.9 mmol). It is stirred for a further 18 h. For working up, it is diluted with dichloromethane (500 ml) and washed with water (3×250 ml). The organic phase is concentrated in vacuo and chromatographed using hexane/ethyl acetate 3:1→2:1→1:1. Yield: 9.3 g, 84%.

$^1$H-NMR (300 MHz, CDCl$_3$): δ=1.09 (d, 3H, 6-H$_{fuc}$), 1.25 (t, 3H, OCH$_2$CH$_3$), 4.14 (q, 2H, OCH$_2$CH$_3$).

c) Synthesis of N-carbonyl-4-carboxypiperidyl-(1→2)-[(α-L-fuco-pyranosyl)-(1→1)]-(1R, 2R)-trans-1,2-cyclohexanediol (3a):

A mixture of compound 2a (9.75 g, 13.6 mmol) and palladium charcoal (10%, 9 g) in methanol/dioxane/glacial acetic acid (50:5:2, 570 ml) is hydrogenated for 24 h under normal pressure in a hydrogen atmosphere. The palladium charcoal is filtered off, and the residue is concentrated and treated with 1M sodium hydroxide solution (100 ml). After 2 h, the mixture is neutralized with Amberlite IR-120 and purified on RP silica gel (C$_{18}$ Bakerbond 60 Å) using water/methanol 9:1→1:9. Compound 3a is obtained (5.18 g, 91%).

$^1$H-NMR (300 MHz, D$_2$O)δ=1.05 (d, 3H, 6-H$_{fuc}$), 1.56 (m, 2H), 1.78 (m, 3H) 2.00 (m, 1H), 2.45 (m, 1H), 2.80 (m, 2H), 4.50 (m, 1H, 2-H$_{cyclohex}$), 4.87 (bs, 1H, 1-H$_{fuc}$).

EXAMPLE 2 a) Synthesis of N-carbonyl-3-[(hydroxymethyl)-piperidyl]-(1→2)-[(2,3,4- tri-O-benzyl-α-L-fucopyranosyl)-(1→1)]-(1R, 2R)-trans-1,2-cyclohexanediol (1b):

Compound 1b is prepared analogously to 3a. For this purpose, 1a is reacted with nitrophenyl chloroformate and 3-(hydroxymethyl)piperidine (Aldrich) is then added. Working up is carried out as described in 3a.

b) Synthesis of N-carbonyl-3-[(p-toluenesulfonyloxymethyl)piperidyl]-(1→2)-[(2,3,4-tri-O-benzyl-α-L-fucopyranosyl)-(1→1)]-(1R, 2R)-trans-1,2-cyclohexanediol (2b):

p-Toluenesulfonyl chloride (277 mg, 1.45 mmol) is added to an ice-cold solution of compound 1b (650 mg, 0.97 mmol) in pyridine (13 ml). After 18 h, dichloromethane (100 ml) is added and the organic phase is washed with sat. sodium chloride solution (2×50 ml). The organic phase is dried over sodium sulfate, filtered and concentrated in vacuo. Flash chromatography (hexane/ethyl acetate 2:1) yields compound 2b (537 mg, 67%).

$^1$H-NMR (300 MHz, CDCl$_3$): δ=1.06 (d, 3H, 6-H$_{fuc}$), 2.04 (s, 3H, CH$_3$).

b) Synthesis of [N-carbonyl-(1,1-dicarbmethoxy-ethyl)-(2→3)-piperidyl]-(1→2)-[(α-L-fucopyranosyl)-(1→1)]-(1R, 2R)-trans-1,2-cyclohexanediol (3b):

A mixture of compound 2b (460 mg, 556 µmol), dimethyl malonate (18 ml), potassium carbonate (1.07 g) and dibenzo-18-crown-6 (264 mg) is stirred at 100° C. for 4 h. For working up, it is diluted with dichloromethane (460 ml) and the organic phase is treated alternately with water and dry ice until the washing water has a neutral reaction. The organic phase is dried over sodium sulfate and concentrated at 80° C. in a high vacuum. Chromatography (hexane/ethyl acetate 2:1) yields compound 3b (367 mg, 84%).

$^1$H-NMR (300 MHz, CDCl$_3$): δ=1.08 (d, 3H, 6-H$_{fuc}$), 3.72 (2 s, 6H, 2 COOCH$_3$).

c) Synthesis of [N-carbonyl-(1,1-dicarboxyethyl)- (2→3) piperidyl]-(1→2)-[(α-L-fucopyranosyl)-(1→1)]-(1R, 2R)-trans-1,2-cyclohexanediol (4b):

Deprotection of 4b takes place as described under 3a.

$^1$H-NMR (300 MHz, D$_2$O): δ=1.09 (d, 3H, 6-H$_{fuc}$), 4.54 (m, 1H, 2-H$_{cyclohex}$), 4.91 (bs, 1H, 1-H$_{fuc}$).

EXAMPLE 3 a) Synthesis of 2-bromo-N-(2-bromoethyl)-N-carbobenzoxyethanamine (1c):

Benzyl chloroformate (1.97 ml, 13.8 mmol) and 1M sodium hydroxide solution is added with vigorous stirring to an ice-cold solution of bis(2-bromoethyl)amine hydrobromide (4.5 g, 14.4 mmol) in water (25 ml) until the pH is just basic (about 24 ml). The mixture is acidified with 1M hydrochloric acid (2 ml) and extracted with ether (3×40 ml). The organic phase is washed with sodium hydrogen carbonate solution and water, dried over magnesium sulfate and concentrated, and the residue is chromatographed (hexane/ethyl acetate 5:1→4:1). Compound 1 c (4.1 g, 81%) is obtained.

$^1$H-NMR (300 MHz, CDCl$_3$): δ=3.43, 3.53 [2 m, 4H, N(CH$_2$—CH$_2$Br)$_2$], 3.73 [m, 4H, N(CH$_2$—CH$_2$Br)$_2$], 5.17 (s, 2H, CH$_2$Ph), 7.36 (m, 5H, Ph).

b) Synthesis of N-carbobenzoxy-4,4-dicarbethoxypiperidine (2c):

Diethyl malonate (303 µl, 2 mmol) is added to a solution of 1c (1.1 g, 3 mmol) in dimethylformamide (1 ml) and the mixture is warmed to 50° C. After addition of sodium hydride (120 mg, 5 mmol), it is stirred for a further 12 h. The mixture is concentrated in a high vacuum and chromatographed using hexane/ethyl acetate 9:2→7:2. Yield 0.5 g, 69%.

$^1$H-NMR (300 MHz, CDCl$_3$): δ=1.25 (t, 6H, 2 CH$_3$), 2.08 (m, 4H, C—CH$_2$—CH$_2$N), 3.52 (m, 4H, C—CH$_2$—CH$_2$N), 4.20 (q, 4H, 2OCH$_2$CH$_3$), 5.12 (s, 2H, CH$_2$Ph), 7.35 (m, 5H, Ph).

c) Synthesis of 4,4-dicarbethoxypiperidine (3c):

A mixture of 2c (778 mg, 2.14 mmol) and palladium charcoal (78 mg) in methanol (10 ml) is hydrogenated under a hydrogen atmosphere for 1 h. For working up, it is filtered and concentrated. 3c (485 mg, 99%) is employed crude in the next stage. $^1$H-NMR (300 MHz, CDCl$_3$):δ=1.26 (t, 6H, 2CH$_3$), 2.06 (m, 4H, C—CH$_2$—CH$_2$N), 2.87 (m, 4H, C—CH$_2$—CH$_2$N), 4.20 (q, 4H, 2OCH$_2$CH$_3$).

d) Synthesis of N-carbonyl-4,4-dicarbethoxypiperidyl-(1→2)-[(2,3,4-tri-O-benzyl-α-L-fucopyranosyl)-(1→1)]-(1R, 2R)-trans-1,2-cyclohexanediol (4c):

Compound 4c is synthesized from 1a and 3c analogously to 2a.

$^1$H-NMR (300 MHz, CDCl$_3$): δ=1.09 (d, 3H, 6-H$_{fuc}$), 1.27 (2t, 6H, 2CH$_3$), 202 (m, 4H, C—CH$_2$—CH$_2$N), 4.2 (2q, 4H, 2OCH$_2$CH$_3$), 7.3 (m, 15H, 3Ph).

e) Synthesis of N-carbonyl-4,4-dicarboxypiperidyl-(1→2)-[(α-L-fucopyranosyl)-(1→1)]-(1R, 2R)-trans-1,2-cyclohexanediol (5c):

Compound 4d is deprotected analogously to 3a.

$^1$H-NMR (300 MHz, D$_2$O): δ=0.95 (d, 3H, 6-H$_{fuc}$), 1.46 (m, 2H), 1.74 (m, 4H), 1.90 (m, 1H), 3.69 (q, 1H, 5-H$_{fuc}$), 4.41 (m, 1H, 2-H$_{cyclohex}$), 4.78 (bs, 1H, 1-H$_{fuc}$).

EXAMPLE 4 a) Synthesis of [(2,3,4-tri-O-acetyl-α-L-rhamnopyranosyl)-(1→1)]-(1R, 2R)-trans-1,2-cyclohexanediol (1d):

A 0.1M trimethylsilyl trifluoromethanesulfonate solution (0.23 mmol) is added dropwise to a mixture of (1R,2R)-trans-1,2-cyclohexanediol (401 mg, 35 mmol) and O-(2,3, 4-tri-O-acetyl-L-rhamnopyranosyl) trichloroacetimidate (1.0 g, 2.3 mmol) in dichloromethane (25 ml). After 20 min, the reaction is terminated with sodium hydrogen carbonate (200 mg), the mixture is filtered, the filtrate is concentrated and the residue is chromatographed using hexane/ethyl acetate 2:1. Yield: 640 mg, 72%. $^1$H-NMR (300 MHz, CDCl$_3$): δ=1.24 (d, 3H, 6-H$_{rham}$), 2.00, 2.05, 2.16 (3S, 9H, 3 OAc), 4.92 (d, 1H, 1-H$_{rham}$), 5.08 (dd, 1H, 4-H$_{rham}$), 5.21 (dd, 1H, 2-H$_{rham}$), 5.32 (dd, 1H, 3-H$_{rham}$).

b) Synthesis of N-carbonyl-4-carbethoxypiperidyl-(1→2)-[(2,3,4-tri-O-acetyl-α-L-rhamnopyranosyl)-(1→1)]-(1R, 2R)-trans-1,2-cyclo-hexanediol (2d):

Compound 2d is synthesized analogously to 2a.

c) Synthesis of N-carbonyl-4-carboxypiperidyl-(1→2)-[(α-L-rhamnopyranosyl)-(1→1)]-(1R,2R)-trans-1,2-cyclohexanediol (3d):

A 1M sodium methoxide solution (1.05 ml) is added to a solution of compound 2d (425 mg, 744 μmol) in methanol (30 ml). After 1 h, the mixture is neutralized with Amberlite IR-120, filtered and concentrated. 1M sodium hydroxide solution (10 ml) is added to the residue. After 1 h, the mixture is again neutralized with Amberlite IR-120, filtered and concentrated. The residue is purified as described in 3a. Yield: 258 mg (83%).

d) Synthesis of N-carbonyl-4-carboxypiperidyl-(1→2)-[(α-L-fuco-pyranosyl)-(1→1)]-(1R,2R)-trans-1,2-cyclopentanediol (1e):

Compound 1e is synthesized analogously to 3a.

EXAMPLE 5 a) Synthesis of N-carbonyl-4-carboxypiperidyl-(1→2)-[(L-threityl)-(1→1)]-(1R, 2R)-trans-1,2-cyclohexanediol (1f):

Compound 1f is prepared analogously to 3a, (1R,2R)-trans-1,2- cyclohexanediol being reacted not with thioethyl O-2,3,4-tri-O-benzyl-α-L-fucopyranoside but with 2,3,4-tri-O-benzyl-1-O-toluenesulfonyl-L-threitol (in toluene/50% sodium hydroxide solution and tetrabutylammonium bromide as a phase transfer catalyst) (see also Example 7)).

EXAMPLE 6 c) Synthesis of [N-carbonyl-(1,1-dicarboxyethyl)-(2→2)-(R or S)-pyrrolidyl]-(1→2)-[(α-fucopyranosyl)-(1→1)]-(1R, 2R)-trans-1,2-cyclohexanediol (1 g):

Compound 1 g is prepared analogously to 4b, 1a being reacted not with 3-hydroxymethylpiperidine but with prolinol (D or L).

EXAMPLE 7 a) Synthesis of N-carbonyl-4-carboxypiperidyl- (1→2)-[(methyl-α-D-mannopyranosyl)-(6→1)]-(1R, 2R)-trans-1,2-cyclohexanediol (1 h):

A solution of methyl 2,3,4-tri-O-benzyl-6-O-toluenesulfonyl-α-D-mannopyranoside (1.19 g, 1.93 mmol) in toluene (10 ml) is added to a mixture of (1R,2R)-trans-1,2-cyclohexanediol (336 mg, 2.894 mmol), toluene (8 ml), tetrabutylammonium bromide (311 mg, 0.97 mmol) and 50% strength sodium hydroxide solution (4.5 ml). The mixture is stirred at 60° C. for 12 h, diluted with ether and washed with water until neutral. Flash chromatography (toluene/acetone 6:1→5:1 yields [(methyl-2,3,4-tri-O-benzyl-α-D-mannopyranosyl)-(6→1)]-(1R,2R)-trans-1,2-cyclohexanediol, which is further processed like compound 1a from Example 1.

EXAMPLE 8 a) Synthesis of N-carbonyl-4-carboxypiperidyl-(1→2)-[(methyl-β-D-galactopyranosyl)-6→1)]-(1R, 2R)-trans-1,2-cyclohexanediol (1i):

Compound 1i is prepared analogously to 1h (Example 7), (1R,2R)-trans-1,2-cyclohexanediol being reacted with methyl 2,3,4-tri-O-benzyl-6-O-toluenesulfonyl-β-D-galactopyranoside in toluene/50% sodium hydroxide solution with tetrabutylammonium bromide as a phase-transfer catalyst and the protected precursor being further processed like 1a from Example 1.

EXAMPLE 9 a) Synthesis of N-carbonyl-4-carboxypiperidyl-(1→2)-[galactopyranosyl-(6→1)]-(1R, 2R)-trans-1,2-cyclohexanediol (1k):

Compound 1k is prepared analogously to 1 h (Example 8), (1R,2R)-trans-1,2-cyclohexanediol being reacted with benzyl 2,3,4-tri-O-benzyl-6-O-trifluoromethanesulfonyl-β-D-galactopyranoside (in dimethylformamide/1.2 equivalents of sodium hydride).

We claim:

1. A compound of the formula

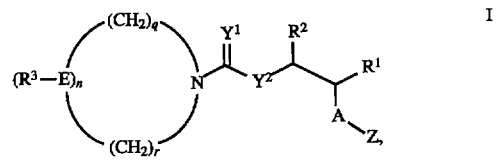

in which

Z is a pyranoside, a pyranosyl radical linked via the C6 position, an alkyl pyranoside linked via the C6 position, a furanoside, a furanosyl radical linked via the C5 position, an alkyl furanoside linked via the C5 position or a polyalcohol which is linked to A via any desired position, A is oxygen, —$CH_2$— or sulfur, $R^1$ and $R^2$ independently of one another are hydrogen, —$(CH_2)_m X^1$ or $CH_2O(CH_2)_m X^2$, where m is an integer from 1 to 20, or together are a five- or six-membered carbo- or heterocycle having at least one of the substituents $R^4$, $R^5$ or $R^6$, E is nitrogen, carbon or —CH—, $R^3$ is —$(CH_2)_p COOH$, (—$COOH)_2$, —$(CH_2)_p CH(COOH)_2$, —$(CH_2)_p CNH_2(COOH)_2$, —$(CH_2)_p C(CH_2-C_6H_5)(COOH)_2$, —$CONHC(COOH)_2$, where p is an integer from 0 to 10, or

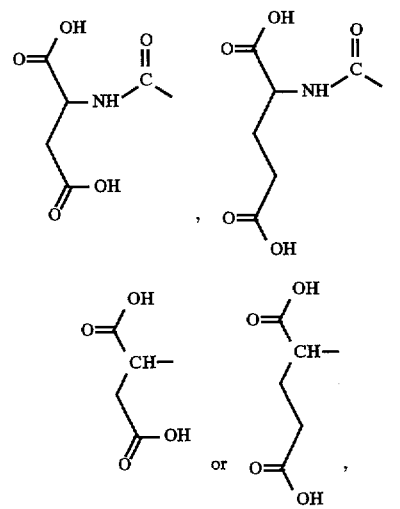

q and r independently of one another are an integer from 0 to 3, n is an integer from 1 to 3, with the proviso that the sum of q, r and n is 4 or 5, $R^4$, $R^5$ and $R^6$ independently of one another are H, OH, —$O(CH_2)_w X^3$ or $CH_2O(CH_2)_w X^4$, where w is an integer from 1 to 18, $Y^1$ and $Y^2$ independently of one another are oxygen, —NH— or sulfur and $X^1$, $X^2$, $X^3$ and $X^4$ independently of one another are hydrogen, —$NH_2$, —COOH, —OH, —$CH_2OH$, $CH_2NH_2$, —$C_1$-$C_{20}$-alkyl or —$C_6$-$C_{10}$-aryl.

2. The compound as claimed in claim 1, wherein $R^1$ and $R^2$ together form a cyclohexane ring.

3. The compound as claimed in claim 1, wherein $R^1$ and $R^2$ together form a cyclopentane ring.

4. The compound as claimed in claim 1, wherein A is oxygen.

5. The compound as claimed in claim 1, wherein $Y_1$ and $Y_2$ are oxygen.

6. The compound as claimed in claim 1, wherein n is 1 and q and r are 2.

7. The compound as claimed in claim 1, wherein n and r are 1 and q is 3.

8. The compound as claimed in claim 1, wherein n is 1, q is 0 and r is 3.

9. The compound as claimed in claim 1, wherein E is —CH—, $R^3$ is —$(CH_2)_p$COOH and p is 0.

10. The compound as claimed in claim 1, wherein E is —CH—, $R^3$ is —$(CH_2)_p$CH(COOH)$_2$ and p is 1.

11. The compound as claimed in claim 1, wherein E is carbon and $R^3$ is (—COOH)$_2$.

12. The compound as claimed in claim 1, wherein Z is a pyranoside.

13. The compound as claimed in claim 12, wherein the pyranoside is L-fucoside, D-mannoside, L-rhamnoside, L-galactoside or L-mannoside.

14. The compound as claimed in claim 13, wherein the pyranoside is L-fucoside.

15. The compound as claimed in claim 14, wherein A, $Y^1$ and $Y^2$ are oxygen, $R^1$ and $R^2$ together form a cyclohexane ring, $R^3$ is $(CH_2)_p$COOH, E is —CH—, n is 1, q and r are 2 and p is 0.

16. The compound as claimed in claim 14, wherein A, $Y^1$ and $Y^2$ are oxygen, $R^1$ and $R^2$ together form a cyclohexane ring, $R^3$ is $(CH_2)_p$CH(COOH)$_2$, E is —CH—, n and r are 1, q is 3 and p is 1.

17. The compound as claimed in claim 14, wherein A, $Y^1$ and $Y^2$ are oxygen, $R^1$ and $R^2$ together form a cyclohexane ring, $R^3$ is (COOH)$_2$, E is carbon, n is 1 and q and r are 2.

18. The compound as claimed in claim 14, wherein A, $Y^1$ and $Y^2$ are oxygen, where $R^1$ and $R^2$ together form a cyclopentane ring, and $R^3$ is $(CH_2)_p$COOH, E is —CH—, p is 0, n is 1 and q and r are 2.

19. The compound as claimed in claim 14, wherein A, $Y^1$ and $Y^2$ are oxygen, where $R^1$ and $R^2$ together form a cyclohexane ring and $R^3$ is $(CH_2)_p$CH(COOH)$_2$, p is 1, E is —CH—, n is 1, q is 0 and r is 3.

20. The compound as claimed in claim 13, wherein the pyranoside is a D-mannoside.

21. The compound as claimed in claim 13, wherein the pyranoside is an L-rhamnoside.

22. The compound as claimed in claim 21, A, $Y^1$ and $Y^2$ are oxygen, $R^1$ and $R^2$ together form a cyclohexane ring, $R^3$ is $(CH_2)_p$COOH, E is —CH—, p is 0, n is and q and r are 2.

23. The compound as claimed in claim 13, wherein the pyranoside is L-galactoside.

24. The compound as claimed in claim 13, wherein the pyranoside is L-mannoside.

25. The compound as claimed in claim 1, wherein Z is a furanoside.

26. The compound as claimed in claim 25, wherein the furanoside is a riboside.

27. The compound as claimed in claim 1, wherein Z is a D-mannosyl radical linked via the C6 position.

28. The compound as claimed in claim 1, wherein Z is a methyl D-mannoside linked via the C6 position.

29. The compound as claimed in claim 1, wherein Z is an L-threito 1-yl radical.

30. The compound as claimed in claim 1, wherein n is 1 and q and r are 2, n and r are 1 and q is 3 or n is 1, q is 0 and r is 3.

31. The compound as claimed in claim 1, wherein E is —CH—, $R^3$ is —$(CH_2)_p$COOH, or —$(CH_2)_p$CH(OOOH)$_2$, and p is 0 or 1.

32. A process for the preparation of a compound as claimed in claim 1, which comprises:

(1) reacting a compound of formula VI wherein $L^4$ leaving group, with a mono- or polycarboxylated cyclic amine or a precursor thereof and;

(2) after elimination of protective groups, to the compound of the formula I, the variables $R^1$, $R^2$, $Y^1$, $Y^2$, A and Z have the meaning defined in claim 1.

33. A pharmaceutical composition a compound as claimed in claim 1 and a pharmaceutically acceptable carrier.

34. A method of inhibiting selectin-mediated cell adhesion, comprising contacting selectin-bearing cells with a compound according to claim 1.

35. A method of treatment of a disease associated with excessive selectin-mediated cell adhesion, comprising administering to a patient in need thereof, an effective amount of a pharmaceutical composition according to claim 33.

36. The method according to claim 35, wherein the disease is a cardiovascular disease.

37. A method of preparing a pharmaceutical composition, comprising contacting a compound according to claim 1 with a pharmaceutically acceptable excipient or additive.

* * * * *